United States Patent [19]

Peterson

[11] 4,125,548

[45] Nov. 14, 1978

[54] 12,13(E)-DIDEHYDRO-13,14-DIHYDRO-9,10-DIDEHYDRO-9-DEOXY-PGD$_1$ COMPOUNDS

[75] Inventor: David C. Peterson, Portage, Mich.

[73] Assignee: The Upjohn Company, Kalamazoo, Mich.

[21] Appl. No.: 809,350

[22] Filed: Jun. 23, 1977

Related U.S. Application Data

[62] Division of Ser. No. 614,244, Sep. 17, 1975.

[51] Int. Cl.$^2$ .............................................. C07C 177/00
[52] U.S. Cl. ................................... 260/408; 260/410; 260/410.5; 260/410.9 R; 260/413; 560/121; 562/503
[58] Field of Search ................... 260/514 D, 408, 410, 260/410.5, 410.9 R, 413; 560/121

[56] References Cited

FOREIGN PATENT DOCUMENTS 835,993 5/1976 Belgium .................................... 260/514

*Primary Examiner*—Robert Gerstl
*Attorney, Agent, or Firm*—Robert A. Armitage

[57] ABSTRACT

Prostaglandin analogs with the following cyclopentane ring structure:

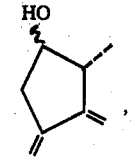

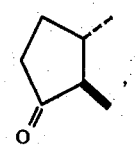

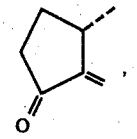

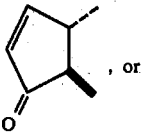

, or

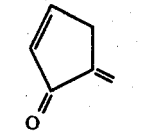

are disclosed along with intermediates useful in their preparation and processes for their preparation. These analogs are useful for some of the same pharmacological purposes as the prostaglandins, particularly and especially as blood platelet aggregation inhibitors.

25 Claims, No Drawings

12,13(E)-DIDEHYDRO-13,14-DIHYDRO-9,10-DIDEHYDRO-9-DEOXY-PGD$_1$ COMPOUNDS

The present application is a divisional application of Ser. No. 614,244, filed Sept. 17, 1975, now pending. United States Ser. No. 809,248, filed June 23, 1977, and also a divisional application of Ser. No. 614,244, has now issued as U.S. Pat. No. 4,099,014.

The present invention relates to prostaglandin analogs, for which the essential material constituting disclosure therefor is incorporated by reference here from U.S. Pat. 4,099,014.

I claim:

1. A prostaglandin analog of the formula

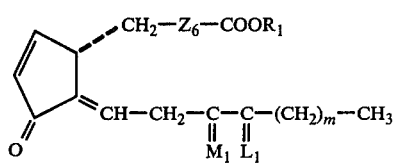

wherein $m$ is one to 5, inclusive; wherein $M_1$ is

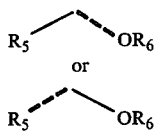

or

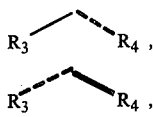

wherein $R_5$ and $R_6$ are hydrogen or methyl, with the proviso that one of $R_5$ and $R_6$ is methyl only when the other is hydrogen;

wherein $L_1$ is

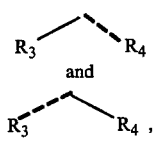

or a mixture of

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and wherein $Z_6$ is $$-(CH_2)_3-(CH_2)_g-CF_2- \quad (1)$$

or $$-(CH_2)_3-(CH_2)_g-CH_2-, \quad (2)$$

wherein $g$ is one, 2, or 3.

2. A compound according to claim 1 wherein $M_1$ is

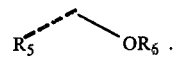

3. A compound according to claim 1, wherein $M_1$ is

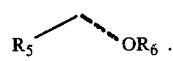

4. A compound according to claim 3, wherein $m$ is 3.

5. A compound according to claim 4, wherein $Z_6$ is $-(CH_2)_3-(CH_2)_g-CH_2-$.

6. A compound according to claim 5, wherein $g$ is 3.

7. A compound according to claim 5, wherein $g$ is one.

8. A compound according to claim 7, wherein $R_5$ and $R_6$ are both hydrogen.

9. A compound according to claim 8, wherein $R_3$ and $R_4$ are both hydrogen.

10. 13,14-Dihydro-12,13(E)-didehydro-9-deoxy-9,10-didehydro-PGD$_1$, a compound according to claim 9.

11. A compound according to claim 8, wherein $R_3$ and $R_4$ are both fluoro.

12. 16,16-Difluoro-13,14-dihydro-12,13(E)-didehydro-9-deoxy-9,10-didehydro-PGD$_1$, a compound according to claim 11.

13. A compound according to claim 4, wherein $Z_6$ is $-(CH_2)_3-(CH_2)_g-CF_2-$ 14. A compound according to claim 13, wherein $g$ is 3.

15. A compound according to claim 14, wherein $R_5$ and $R_6$ are both hydrogen.

16. A compound according to claim 15, wherein $R_3$ and $R_4$ are both hydrogen.

17. 2a,2b-Dihomo-2,2-difluoro-13,14-dihydro-12,13(E)-didehydro9-deoxy-9,10-didehydro-PGD$_1$, a compound according to claim 15.

18. A compound according to claim 15, wherein $R_3$ and $R_4$ are both fluoro.

19. 2a,2b-Dihomo-2,2,16,16-tetrafluoro-13,14-dihydro12,13(E)-didehydro-9-deoxy-9,10-didehydro-PGD$_1$, a compound according to claim 17.

20. A compound according to claim 13, wherein $g$ is one.

21. A compound according to claim 20, wherein $R_5$ and $R_6$ are both hydrogen.

22. A compound according to claim 21, wherein $R_3$ and $R_4$ are both hydrogen.

23. 2,2-Difluoro-13,14-dihydro-12,13(E)-didehydro-9-deoxy-9,10-didehydro-PGD$_1$, a compound according to claim 22.

24. A compound according to claim 21, wherein $R_3$ and $R_4$ are both fluoro.

25. 2,2,16,16-Tetrafluoro-13,14-dihydro-12,13(E)-didehydro-9-deoxy-9,10-didehydro-PGD$_1$, a compound according to claim 24.

* * * * *

UNITED STATES PATENT OFFICE
CERTIFICATE OF CORRECTION

Patent No. 4,125,548  Dated November 14, 1978

Inventor(s) David C. Peterson

It is certified that error appears in the above-identified patent and that said Letters Patent are hereby corrected as shown below:

[References Cited] should include
-- 3,878,239  4/75  Hayashi, et al.  260/514
   4,015,184  4/77  Morton, et al.   260/408 --

Column 2, line 45, "-didehydro9-deoxy" should read -- -didehydro-9-deoxy --;
lines 49-50, "-didehydro12,13(E)-" should -- -didehydro-12,13(E)- --;
line 57, "didehydro-b" should read -- didehydro- --.

Signed and Sealed this

Sixth Day of March 1979

[SEAL]

Attest:

RUTH C. MASON
Attesting Officer

DONALD W. BANNER
Commissioner of Patents and Trademarks